United States Patent [19]

Calvin et al.

[11] 4,348,486

[45] Sep. 7, 1982

[54] PRODUCTION OF METHANOL VIA CATALYTIC COAL GASIFICATION

[75] Inventors: William J. Calvin, Convent Station; Stuart S. Goldstein, Kinnelon; Harry A. Marshall, Madison, all of N.J.

[73] Assignee: Exxon Research and Engineering Co., Florham Park, N.J.

[21] Appl. No.: 296,713

[22] Filed: Aug. 27, 1981

[51] Int. Cl.$^3$ .................. C07C 27/06; C07L 31/04
[52] U.S. Cl. .................. 518/704; 515/705; 515/713; 515/714; 48/197 R; 48/202; 62/56; 62/9; 62/24; 62/32
[58] Field of Search ............. 518/704, 705, 713, 714

[56] References Cited

U.S. PATENT DOCUMENTS 3,993,457 11/1976 Cahn et al. .................. 48/197 R
4,211,669 7/1980 Eakman et al. ............... 252/373

*Primary Examiner*—Howard T. Mars
*Attorney, Agent, or Firm*—Yale S. Finkle

[57] ABSTRACT

Methanol is produced by gasifying a carbonaceous feed material with steam in the presence of a carbon-alkali metal catalyst and added hydrogen and carbon monoxide at a temperature between about 1000° F. and about 1500° F. and at a pressure in excess of about 100 psia to produce a raw product gas comprising methane, steam, carbon dioxide, carbon monoxide, hydrogen and hydrogen sulfide; withdrawing the raw product gas from the gasifier and treating it for the removal of steam, particulates, hydrogen sulfide and carbon dioxide to produce a treated gas containing primarily carbon monoxide, hydrogen and methane; separating the treated gas into a methane-rich gas stream and a gas stream containing primarily carbon monoxide and hydrogen; passing the methane-rich gas stream to a steam reforming furnace wherein a portion of the methane is reacted with steam to produce hydrogen and carbon monoxide which is then passed from the steam reforming furnace into the gasifier; passing the gas stream containing primarily carbon monoxide and hydrogen to a methanol synthesis reactor where the carbon monoxide is reacted with the hydrogen in the presence of a methanol synthesis catalyst to form methanol; recovering methanol product from the effluent exiting the methanol synthesis reactor thereby leaving a gas comprised of carbon monoxide, hydrogen, methane and carbon dioxide; and recycling at least a portion of this gas to the separation step of the process.

11 Claims, 1 Drawing Figure

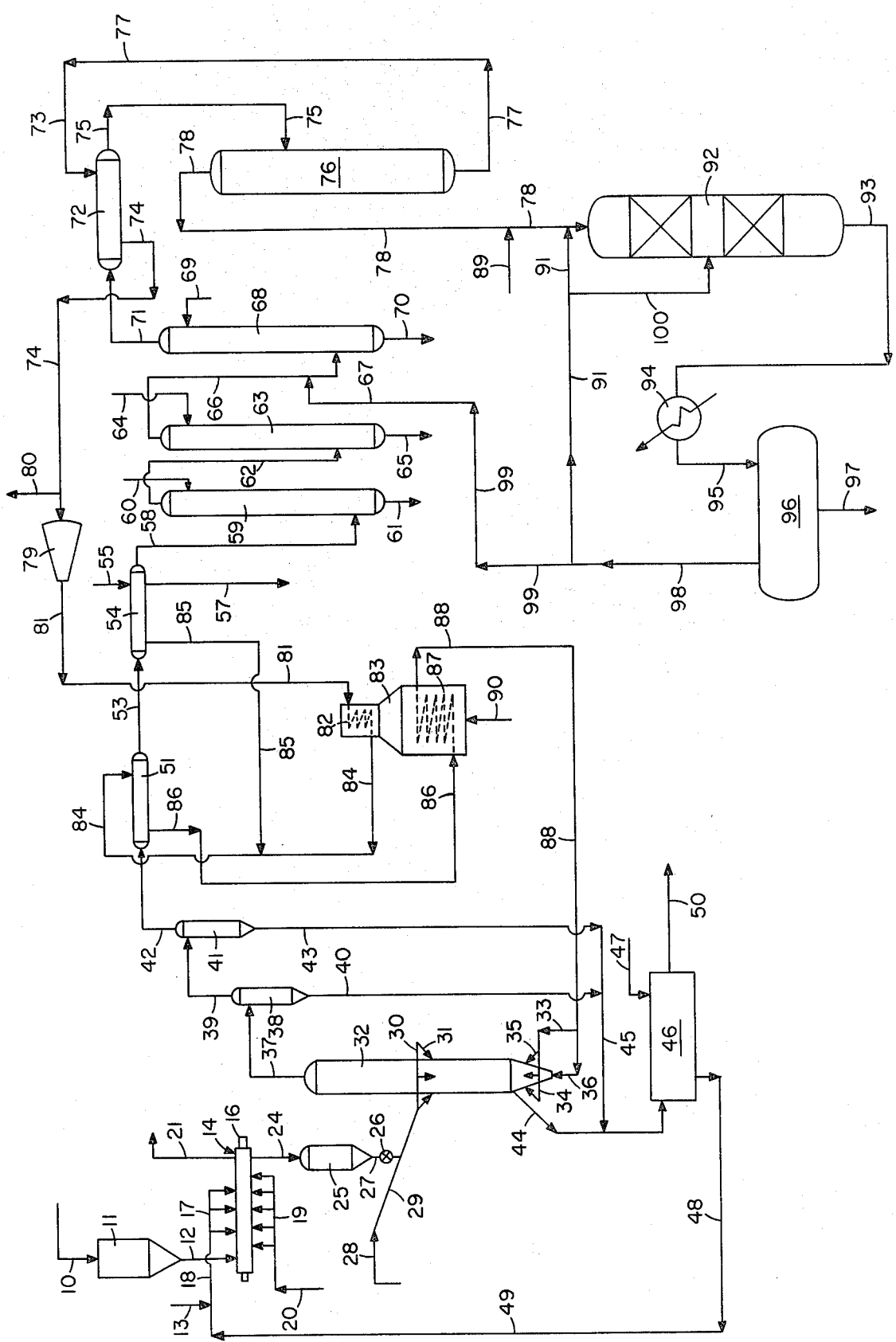

PRODUCTION OF METHANOL VIA CATALYTIC COAL GASIFICATION

BACKGROUND OF THE INVENTION

This invention relates to the gasification of coal and similar carbonaceous materials and is particularly concerned with producing methanol by integrating a catalytic gasification process carried out in the presence of a carbon-alkali metal catalyst with a methanol synthesis process.

Existing and proposed processes for the manufacture of synthetic gaseous fuels from coal or similar carbonaceous materials normally require the reaction of carbon with steam, alone or in combination with oxygen, at temperatures between about 1200° F. and 2500° F. to produce a gas which may contain some methane but consists primarily of hydrogen and carbon monoxide. This gas can be used directly as a synthesis gas or a fuel gas with little added processing or can be reacted with additional steam to increase the hydrogen-to-carbon monoxide ratio and then fed to a catalytic methanation unit for reaction with carbon monoxide and hydrogen to produce methane. It has been shown that processes of this type can be improved by carrying out the initial gasification step in the presence of a catalyst containing an alkali metal constituent. The alkali metal constituent accelerates the steam-carbon gasification reaction and thus permits the generation of synthesis gas at somewhat lower temperatures than would otherwise be required. Processes of this type are costly because of the large quantities of heat that must be supplied to sustain the highly endothermic steam-carbon reaction. One method of supplying this heat is to inject oxygen directly into the gasifier and burn a portion of the carbon in the feed material being gasified. This method is highly expensive in that it requires the existence of a plant to manufacture the oxygen. Other methods for supplying the heat have been suggested, but these, like that of injecting oxygen, are expensive.

It has been found that difficulties associated with processes of the type described above, can largely be avoided by carrying out the reaction of steam with carbon in the presence of a carbon-alkali metal catalyst and substantially equilibrium quantities of added hydrogen and carbon monoxide. Laboratory work and pilot plant tests have shown that catalysts produced by the reaction of carbon and alkali metal compounds such as potassium carbonate to form carbon-alkali metal compounds or complxes will, under the proper reaction conditions, equilibrate the gas phase reactions occurring during gasification to produce methane and at the same time supply substantial amounts of exothermic heat within the gasifier. This additional exothermic heat of reaction essentially balances the overall endothermicity of the reactions involving solid carbon and thus results in a substantially thermoneutral process in which the injection of large amounts of oxygen or the use of other expensive methods of supplying heat are eliminated.

The catalytic effect of carbon-alkali metal catalysts on the gas phase reactions, as distinguished from the solid-gas reactions or the reactions of carbon with steam, hydrogen or carbon dioxide, allows the following exothermic reactions to contribute substantially to the presence of methane in the effluent gas and drastically reduces the endothermicity of the overall reaction:

$$2CO + 2H_2 \rightarrow CO_2 + CH_4 \text{ (exothermic)} \quad (1)$$

$$CO + 3H_2 \rightarrow H_2O + CH_4 \text{ (exothermic)} \quad (2)$$

$$CO_2 + 4H_2 \rightarrow 2H_2O + CH_4 \text{ (exothermic)} \quad (3)$$

Under the proper operating conditions, these reactions can be made to take place within the gasification zone and supply large amounts of methane and additional exothermic heat which would otherwise have to be supplied by the injection of oxygen or other means. Laboratory and pilot plant tests have shown that constituents of the raw product gas thus produced are present in equilibrium concentrations at reaction conditions and consist primarily of hydrogen, carbon monoxide, carbon dioxide, methane and steam.

It has been proposed in U.S. Pat. No. 4,211,669 to utilize steam gasification in the presence of a carbon-alkali metal catalyst to produce a chemical synthesis gas by treating the raw product gas withdrawn from the gasifier for removal of steam and acid gases, principally carbon dioxide and hydrogen sulfide; cryogenically separating carbon monoxide and hydrogen in amounts equivalent to their equilibrium concentration in the raw product gas from the methane in the treated gas; withdrawing the carbon monoxide and hydrogen as chemical synthesis product gas; contacting the methane with steam in a steam reformer under conditions such that at least a portion of the methane reacts with steam to produce hydrogen and carbon monoxide; and passing the effluent from the reformer into the gasifier. The reformer effluent will normally contain carbon monoxide and hydrogen in amounts equivalent to the equilibrium quantities of those gases present in the raw product gas and will therefore supply the substantially equilibrium quantities of hydrogen and carbon monoxide required in the gasifier along with the carbon-alkali metal catalyst and steam to produce the thermoneutral reaction that results in the formation of essentially methane and carbon dioxide.

As evidenced by U.S. Pat. Nos. 4,094,650 and 4,118,204, respectively, it has also been proposed to utilize steam gasification of a carbonaceous feed material in the presence of a carbon-alkali metal catalyst to produce both a high BTU and an intermediate BTU product gas. These processes are somewhat similar to the one described in U.S. Pat. No. 4,211,669. In the process disclosed in U.S. Pat. No. 4,094,650, the methane from the cryogenic separation step is recovered as product and the carbon monoxide and hydrogen are recycled to the gasifier to provide the required equilibrium quantities of hydrogen and carbon monoxide. In the process described in U.S. Pat. No. 4,118,204, the cryogenic separation step is eliminated and a portion of the carbon monoxide, hydrogen and methane exiting the acid gas removal step is recovered as the intermediate BTU product gas and the remainder is passed through a steam reformer to convert the methane into carbon monoxide and hydrogen. The effluent from the reformer is then passed into the gasifier to supply the required amounts of carbon monoxide and hydrogen.

Although the above-described catalytic gasification processes result in the substantially thermoneutral reaction of steam with carbon to form a raw product gas containing equilibrium quantities of carbon monoxide, carbon dioxide, hydrogen, steam and methane by recycling carbon monoxide and hydrogen in quantities equivalent to their concentration in the raw product gas to the gasifier and are therefore significant improvements over previously proposed non-catalytic and catalytic processes, they have one major disadvantage. None of the processes can be operated in a manner to produce liquid hydrocarbons. Since there may be a great need in the future for storable synthetic liquids that can be used to fuel vehicles, it may be highly desirable to utilize the thermoneutral process for gasifying carbonaceous materials described above in a manner which would allow the production of liquids instead of gases.

SUMMARY OF THE INVENTION

This invention provides a process for producing methanol by the substantially thermoneutral reaction of steam with coal, petroleum coke, heavy oil, residua and other carbonaceous feed materials in the presence of a carbon-alkali metal catalyst and added hydrogen and carbon monoxide. In accordance with the invention, it has now been found that methanol can be produced by gasifying a carbonaceous feed material with steam in a gasification zone at a temperature between about 1000° F. and about 1500° F. and at a pressure in excess of about 100 psia in the presence of a carbon-alkali metal catalyst and added hydrogen and carbon monoxide, thereby producing an effluent gas containing methane, carbon monoxide, steam, hydrogen, carbon dioxide and hydrogen sulfide. The effluent gas is withdrawn from the gasification zone and treated for the removal of particulates, steam, carbon dioxide and hydrogen sulfide to produce a treated gas containing primarily carbon monoxide, hydrogen and methane. The treated gas is then passed to a separation zone where it is divided into a methane-rich gas stream and a gas stream containing primarily carbon monoxide and hydrogen. The methane-rich gas stream is contacted with steam in a steam reforming zone under conditions such that at least a portion of the methane reacts with the steam to produce carbon monoxide and hydrogen. The effluent from the steam reforming zone is then passed into the gasification zone to supply the required amounts of added hydrogen and carbon monoxide. The gas stream containing primarily carbon monoxide and hydrogen produced in the separation zone is then passed to a methanol synthesis zone wherein a portion of the carbon monoxide and hydrogen is reacted in the presence of a methanol synthesis catalyst to form methanol. The effluent gas from the methanol synthesis zone is treated to recover methanol product thereby leaving a gas comprised primarily of carbon monoxide, hydrogen, methane and carbon dioxide. At least a portion of this gas, which portion is commonly referred to as purge gas, is normally treated to remove carbon dioxide and the resultant treated purge gas is recycled to the separation zone of the process. The recycling of a portion of the gas produced by removing methanol from the effluent exiting the methanol synthesis zone to the separation zone results in the removal of the methane from the recycled gas and the subsequent passage of the removed methane to the steam reforming zone. The carbon monoxide and hydrogen which was originally present in the recycled gas is passed again through the methanol synthesis zone, thereby increasing methanol yields without sacrificing overall process efficiency.

In a preferred embodiment of the invention, the portion of the gas left after the methanol is recovered from the methanol synthesis zone effluent that is not recycled to the separation zone of the process is recycled directly to the methanol synthesis zone without first being treated to remove carbon dioxide. In addition, it is preferable that the carbon dioxide be removed from the portion of the gas that is recycled to the separation zone by passing this gas through the carbon dioxide removal step of the process together with the effluent from the gasification zone. In the preferred embodiment of the invention, the methane-rich stream produced in the separation zone is normally used as part of the fuel for the steam reforming zone. It may also be preferable in some cases to add a portion of the carbon dioxide removed from the gasification zone effluent to the methanol synthesis zone feed in order to adjust the carbon oxides to hydrogen ratio and/or to activate the methanol synthesis catalyst. It is normally desirable that the steam reforming zone effluent contain carbon monoxide and hydrogen in amounts equivalent to the quantities of those gases present in the effluent gas withdrawn from the gasification zone so that the effluent from the steam reforming zone will supply the quantities of hydrogen and carbon monoxide required in the gasification zone along with the carbon-alkali metal catalyst and steam to produce the thermoneutral reaction that results in the formation of essentially methane and carbon dioxide.

The process of the invention provides a highly efficient method of integrating a thermoneutral gasification process with a methanol synthesis process in order to produce methanol and thus has many advantages over thermoneutral gasification processes in the past which could be used only to produce gaseous products.

BRIEF DESCRIPTION OF THE DRAWING

The drawing is a schematic flow diagram of a process carried out in accordance with the invention for the production of methanol via the catalytic gasification of coal or similar carbonaceous solids.

DESCRIPTION OF THE PREFERRED EMBODIMENTS

The process depicted in the drawing is one for the production of methanol by the gasification of bituminous coal, subbituminous coal, lignitic coal, coal char, coke, liquefaction bottoms, oil shale and similar carbonaceous solids with steam at a high temperature in the presence of a carbon-alkali metal catalyst prepared by impregnating the feed solids with a solution of an alkali metal compound or mixture of such compounds and thereafter heating the impregnated material to a temperature sufficient to produce an interaction between the alkali metal and the carbon present. The solid feed material that has been crushed to a particle size of about 8 mesh or smaller on the U.S. Sieve Series Scale is passed into line 10 from a feed preparation plant or storage facility that is not shown in the drawing. The solids introduced into line 10 are fed into a hopper or similar vessel 11 from which they are passed through line 12 into feed preparation zone 14. This zone contains a screw conveyor or similar device, not shown in the drawing, that is powered by a motor 16, a series of spray nozzles or similar devices 17 for the spraying of an alkali metal-containing solution supplied through line 18 onto the solids as they are moved through the preparation zone by the conveyor, and a similar set of nozzles or the like 19 for the introduction of a hot dry gas, such as flue gas, into the preparation zone. The hot gas, supplied through line 20, serves to heat the impregnated solids and drive off the moisture. A mixture of water vapor and gas is withdrawn from zone 14 through line 21 and passed to a condenser, not shown, from which water may be recovered for use as makeup or the like. The majority of the alkali metal-containing solution is recycled through line 49 from the alkali metal recovery portion of the process, which is described in more detail hereinafter. Any makeup alkali metal solution required may be introduced into line 18 via line 13.

It is preferred that sufficient alkali metal-containing solution be introduced into preparation zone 14 to provide from about 5 to about 50 weight percent of an alkali metal compound or mixture of such compounds on the coal or other carbonaceous solids. From about 10 to about 30 percent is generally adequate. The dried impregnated solid particles prepared in zone 14 are withdrawn through line 24 and passed to a closed hopper or similar vessel 25 from which they are discharged through a star wheel feeder or equivalent device 26 in line 27 at an elevated pressure sufficient to permit their entrainment into a stream of high pressure steam, recycle product gas, inert gas or other carrier gas introduced into line 29 via line 28. The carrier gas and entrained solids are passed through line 29 into manifold 30 and fed from the manifold through lines 31 and nozzles, not shown in the drawing, into gasifier 32. In lieu of or in addition to hopper 25 and star wheel feeder 26, the feed system may employ parallel lock hoppers, pressurized hoppers, aerated standpipes operated in series, or other apparatus to raise the input feed solids stream to the required pressure level.

Gasifier 32 contains a fluidized bed of carbonaceous solids extending upward within the vessel above an internal grid or similar distribution device not shown in the drawing. The bed is maintained in the fluidized state by means of steam, hydrogen and carbon monoxide introduced through line 33, manifold 34 and peripherally spaced injection lines and nozzles 35, and through bottom inlet line 36. The particular injection system shown in the drawing is not critical and hence other methods for injecting the steam, hydrogen and carbon monoxide may be employed. In some instances, for example, it may be preferred to introduce the gases through multiple nozzles to obtain more uniform distribution of injected fluid and reduce the possibility of channeling and related problems.

Within the fluidized bed in gasifier 32, the carbonaceous solids impregnated with the alkali metal compound or mixture of such compounds are subjected to a temperature within the range between about 1000° F. and about 1500° F., preferably between about 1200° F. and 1400° F., and to a pressure between about 100 psia and about 1500 psia, preferably between about 200 psia and about 800 psia. Under such conditions the alkali metal constituents interact with the carbon in the carbonaceous solids to form a carbon-alkali metal catalyst, which will under proper reaction conditions equilibrate the gas phase reactions occurring during gasification to produce additional methane and at the same time supply substantial amounts of additional exothermic heat in situ. Due to the gas phase equilibrium conditions existing as a result of the carbon-alkali metal catalyst and due to the presence of equilibrium quantities of hydrogen and carbon monoxide injected with the steam near the lower end of the bed, the net reaction products will normally consist essentially of methane and carbon dioxide. Competing reactions that in the absence of the catalyst and the hydrogen and carbon monoxide would ordinarily tend to produce additional hydrogen and carbon monoxide are suppressed. At the same time, substantial quantities of exothermic heat are released as a result of the reaction of hydrogen with carbon oxides and the reaction of carbon monoxide with steam. This exothermic heat tends to balance the endothermic heat consumed by the reaction of the steam with carbon, thereby producing an overall thermoneutral reaction. So far as the heat of reaction is concerned, the gasifier is therefore largely in heat balance. The heat employed to preheat the feed coal to the reaction temperature and compensate for heat losses from the gasifier is supplied for the most part by excess heat in the gases introduced into the gasifier through lines 35 and 36. In the absence of the exothermic heat provided by the catalyzed gas phase reactions, these gases would have to be heated to substantially higher temperatures than those employed here.

The carbon-alkali metal catalyst utilized in the process of the invention is prepared by heating an intimate mixture of carbon and an alkali metal constituent to an elevated temperature, preferably above 800° F. In the process shown in the drawing and described above, the intimate mixture is prepared by impregnating the carbonaceous feed material with an alkali metal-containing solution and then subjecting the impregnated solids to a temperature above 800° F. in the gasifier itself. It will be understood that the alkali metal catalyst utilized in the process of this invention can be prepared without impregnation onto the carbonaceous solids to be gasified, and without heating in the gasifier. The heating step, for example, may be carried out in a solid feed preparation zone or in an external heater. The carbonaceous solids used will, in most instances, be the ones which are to be gasified but in some variations of the process carbonaceous materials other than the feed solids may be used. In some cases, inert carriers having carbon deposited on their outer surface may be used. Suitable inert carriers include silica, alumina, silica-alumina, zeolites, and the like. The catalyst particles, whether composed substantially of carbon and an alkali metal constituent or made up of carbon and an alkali metal constituent deposited on an inert carrier, may range from fine powders to coarse lumps, particles between about 4 and about 100 mesh on the U.S. Sieve Series Scale generally being preferred.

Any of a variety of alkali metal constituents or mixtures thereof can be used in preparing the carbon-alkali metal catalyst. Suitable constituents include the alkali metals themselves and alkali metal compounds such as alkali metal carbonates, bicarbonates, formates, oxalates, hydroxides, sulfides, and mixtures of these and other similar compounds. All of these are not equally effective and hence a catalyst prepared from certain alkali metal constituents can be expected to give somewhat better results under certain conditions than do others. In general, cesium, potassium, sodium and lithium salts derived from organic or inorganic acids having ionization constants less than about $1 \times 10^{-3}$ and alkali metal hydroxides are preferred. The cesium compounds are the most effective, followed by the potassium, sodium and lithium compounds, in that order. Because of their high activity, relatively low cost compared to cesium compounds, and ready availability, potassium compounds or sodium compounds are generally employed. Potassium carbonate and potassium hydroxide are especially effective.

In the embodiment of the invention shown in the drawing, alkali metal constituents and the carbonaceous solids are combined to form an intimate mixture by dissolving water soluble alkali metal compounds in an aqueous carrier, impregnating the carbonaceous solids with the resulting aqueous solution by soaking or spraying the solution onto the particles, and thereafter drying the solids. It will be understood that other methods of forming such an intimate mixture may be used. For example, in some cases the carbonaceous material can be impregnated by suspending a finely divided alkali metal or alkali metal compound in a hydrocarbon solvent or other inert liquid carrier of suitably low viscosity and high volatility and thereafter treating the solids with the liquid containing the alkali metal constituent. In other cases, it may be advantageous to pelletize a very finely divided alkali metal or alkali metal compound with carbon in an oil or similar binder and then heat the pellets to an elevated temperature. Other catalyst preparation methods, including simply mixing finely divided carbonaceous material with a powdered alkali metal salt and thereafter heating the mixture to the desired temperature, can, in some cases, also be used.

The mechanisms which take place as the result of combining the carbonaceous solids and alkali metal constituents and then heating them to elevated temperatures are not fully understood. Apparently, the alkali metal reacts with the carbon to form carbon-alkali metal compounds and complexes. Studies have shown that neither the carbonaceous solids nor the alkali metal constituents alone are fully effective for establishing equilibrium conditions for gas phase reactions involving steam, hydrogen, carbon monoxide, carbon dioxide and methane and that catalytic activity is obtained only when a compound or complex of the carbon and alkali metal is present in the system. Both constituents of the catalyst are therefore necessary. Experience has shown that these catalysts are resistent to degradation in the presence of sulfur compounds, that they resist sintering at high temperatures, and that they bring gas phase reactions involving the gases normally produced during coal gasification into equilibrium. As a result of these and other beneficial properties, these catalysts have pronounced advantages over other catalysts employed in the past.

Referring again to the drawing, the gas leaving the fluidized bed in gasifier 32 passes through the upper section of the gasifier, which serves as a disengagement zone where the particles too heavy to be entrained by the gas leaving the vessel are returned to the bed. If desired, this disengagement zone may include one or more cyclone separators or the like for removing relatively large particles from the gas. The gas withdrawn from the upper part of the gasifier through line 37 will normally contain an equilibrium mixture at gasification temperature and pressure of methane, carbon dioxide, hydrogen, carbon monoxide and unreacted steam. Also present in this gas are hydrogen sulfide, ammonia and other contaminants formed from the sulfur and nitrogen contained in the feed material, and entrained fines. This raw product gas is introduced into cyclone separator or similar device 38 for removal of the larger fines. The overhead gas then passes through line 39 into a second separator 41 where smaller particles are removed. The gas from which the solids have been separated is taken overhead from separator 41 through line 42 and the fines are discharged downward through dip legs 40 and 43. These fines may be returned to the gasifier or passed to the alkali metal recovery portion of the process.

In the system shown in the drawing, a stream of high ash content char particles is withdrawn through line 44 from gasifier 32 in order to control the ash content of the system and permit the recovery and recycle of alkali metal constituents of the catalyst. The solids in line 44, which may be combined with fines recovered from the gasifier overhead gas through dip legs 40 and 43 and line 45, are passed to alkali metal recovery unit 46. The recovery unit will normally comprise a multistage countercurrent leaching system in which the high ash content particles are countercurrently contacted with water introduced through line 47. An aqueous solution of alkali metal compounds is withdrawn from the unit through line 48 and recycled through lines 49, 18 and 17 to feed preparation zone 14. Ash residues from which soluble alkali metal compounds have been leached are withdrawn from the recovery unit through line 50 and may be disposed of as land fill or further treated to recover additional alkali metal constituents.

The gas leaving separator 41 is passed through line 42 to gas-gas heat exchanger 51 where it is cooled by indirect heat exchange with a gaseous mixture containing methane and steam introduced through line 84. The cooled gas is then passed through line 53 into waste heat boiler 54 where it is further cooled by indirect heat exchange with water introduced through line 55. Sufficient heat is transferred from the gas to the water to convert it into steam, which is withdrawn through line 85. During this cooling step, unreacted steam in the gas from exchanger 51 is condensed out and withdrawn as condensate through line 57. The cool gas exiting waste heat boiler 54 through line 58 is passed to water scrubber 59. Here the gas stream passes upward through the scrubber where it comes in contact with water injected into the top of the scrubber through line 60. The water removes residual particulates and absorbs ammonia and a portion of the hydrogen sulfide in the gas stream, and is withdrawn from the bottom of the scrubber through line 61 and passed to downstream units for further processing. The water scrubbed gas stream is withdrawn from the scrubber through line 62 and is now ready for treatment to remove bulk amounts of hydrogen sulfide and carbon dioxide.

The gas stream is passed from water scrubber 59 through line 62 into the bottom of hydrogen sulfide absorber 63. Here the gas passes upward through the contacting zone in the absorber where it comes in contact with a downflowing stream of a solvent introduced into the upper part of the absorber through line 64. The solvent will normally be a compound that under certain operating conditions will selectively absorb hydrogen sulfide in preference to carbon dioxide. Examples of such solvents include the dimethyl ether of polyethylene glycol, methanol and the like. If desired, the absorber may be provided with spray nozzles, perforated plates, bubble cap plates, packing or other means for promoting intimate contact between the gas and the solvent. As the gas rises through the contacting zone, substantially all of the hydrogen sulfide and a portion of the carbon dioxide are absorbed by the solvent, which exits the scrubber through line 65. The spent solvent containing primarily hydrogen sulfide and small concentrations of other contaminants is passed through line 65 to a stripper, not shown in the drawing, where it is contacted with steam or other stripping gas to remove the hydrogen sulfide and other absorbed contaminants and thereby regenerate the solvent. The regenerated solvent may then be reused by injecting it back into the top of the absorber via line 64.

A gas containing essentially methane, hydrogen, carbon monoxide and carbon dioxide is withdrawn overhead from hydrogen sulfide absorber 63 through line 66. This gas is combined with a recycle purge gas introduced into line 66 through line 67. The recycle purge gas, which will contain carbon monoxide and hydrogen along with methane and carbon dioxide, is produced in downstream portions of the process which are described in detail hereinafter. The combined gas stream is then passed into the bottom of carbon dioxide absorber 68. Here, the mixture of gases passes upward through the contacting zone in the absorber where it comes in contact with a downflowing stream of solvent introduced into the top portion of the absorber through line 69. Normally, the solvent will be the same solvent that is used in hydrogen sulfide absorber 63. Absorber 68 will be operated under conditions such that the solvent absorbs almost all of the carbon dioxide from the mixture of gases passing upward through the contacting zone in the absorber. If desired, however, a different solvent than the one used in hydrogen sulfide absorber 63 may be used in absorber 68. Spent solvent containing primarily carbon dioxide and small amounts of other contaminants is withdrawn from the absorber through line 70 and passed to a stripper, not shown in the drawing, where it is contacted with steam or other stripping gas to remove the carbon dioxide and other absorbed contaminants and thereby regenerate the solvent. The regenerated solvent may then be reused by injecting it back into the top of the absorber via line 69. A clean gas having an intermediate BTU heating value containing essentially methane, hydrogen and carbon monoxide is withdrawn overhead from the carbon dioxide absorber through line 71.

The intermediate BTU gas withdrawn overhead from carbon dioxide absorber 68 is introduced into the heat transfer unit 72 where it passes in indirect heat exchange with liquid methane introduced through line 73. The methane vaporizes within the heat transfer unit and is discharged as a gas through line 74. The vaporizing methane chills the intermediate BTU gas, which is primarily composed of methane, hydrogen and carbon monoxide, to a low temperature approaching that required for liquefaction of the methane contained in the gas, after which the chilled gas is passed through line 75 into cryogenic distillation unit 76. Here the gas is further cooled by conventional means until the temperature reaches a value sufficiently low to liquefy the methane under the pressure conditions existing in the unit. Compressors and other auxiliaries associated with the cryogenic distillation unit are not shown. The amount of pressure required for the liquefaction step will depend in part upon the pressure at which the gasifier is operated and the pressure losses which are incurred in the various portion of the system. A liquid stream containing greater than about 95 weight percent methane is taken off from the cryogenic unit through line 77 and passed through line 73 into heat transfer unit 72 as described earlier. A mixture of hydrogen, carbon monoxide and methane is withdrawn overhead from the cryogenic distillation unit through line 78. The cryogenic unit is normally operated and designed in such a manner that the gas removed overhead will contain between about 2 and about 15 mole percent methane. It will be understood that the cryogenic unit does not necessarily have to be a distillation column and instead can be any type of cryogenic unit in which a majority of the carbon monoxide and hydrogen is separated from the methane in the gas that is fed to the unit. For example, the unit could be a simple one-stage cryogenic flash in which case the effluent removed in line 77 will be methane-rich and will contain a significant amount of dissolved carbon monoxide and hydrogen.

The recycle methane-rich gas removed from heat transfer unit 72 through line 74 is passed to compressor 79 where its pressure is increased to a value from about 25 psi to about 150 psi above the operating pressure in gasifier 32. Under some conditions, it may be desirable to withdraw a portion of this methane-rich gas from line 74 through line 80 for use as fuel in the process or as a high BTU or intermediate BTU by-product gas. The actual heat content of the by-product gas will depend upon the type of cryogenic separation unit 76 that is utilized in the process. If a cryogenic distillation column is used, the by-product gas will normally contain greater than about 95 weight percent methane along with carbon monoxide and hydrogen. If a less efficient separation method is employed, the by-product gas will contain greater amounts of carbon monoxide and hydrogen and will normally be of an intermediate BTU heating value.

The pressurized gas withdrawn from compressor 79 through line 81 is passed through tubes 82 located in the convection section of steam reforming furnace 83. Here, the high pressure gas picks up heat via indirect heat exchange with the hot flue gases generated in the furnace. The methane-rich gas is removed from tubes 82 through line 84 and mixed with steam, which is generated in waste heat boiler 54 and injected into line 84 via line 85. The mixture of methane-rich gas and steam is then passed through line 84 into gas-gas heat exchanger 51 where it is heated by indirect heat exchange with the gasifier raw product gas removed from separator 41. The heated mixture is removed from exchanger 51 and passed through line 86 into steam reforming furnace 83.

The preheated mixture of steam and methane-rich gas in line 86 is introduced into the internal tubes 87 of the steam reforming furnace where the methane and steam react with one another in the presence of a conventional steam reforming catalyst. The catalyst will normally consist of metallic constituents supported on an inert carrier. The metallic constituent will normally be selected from Group VI-B and the iron group of the Periodic Table of Elements and may be chromium, molybdenum, tungsten, nickel, iron or cobalt and may include small amounts of potassium carbonate or a similar compound as a promoter. Suitable inert carriers include silica, alumina, silica-alumina, zeolites and the like.

The reforming furnace is operated under conditions such that the methane in the feed gas will react with steam in the tubes 87 to produce hydrogen and carbon monoxide according to the following equation:

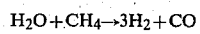

$$H_2O + CH_4 \rightarrow 3H_2 + CO$$

The temperature in the reforming furnace will normally be maintained between about 1200° F. and about 1800° F., preferably between about 100° F. and about 300° F. above the temperature in gasifier 32. The pressure will range between about 10 and about 30 psi above the pressure in the gasifier. The mole ratio of steam to methane introduced into the reactor will range between about 2:1 and about 15:1, preferably between about 3:1 and about 7:1. The reforming furnace is preferably fired by a portion of the methane-rich gas removed from heat transfer unit 72. The required amount of gas is withdrawn from line 74 through line 80 and passed directly to the firebox in the steam reforming furnace via line 90.

The gaseous effluent stream from the steam reforming furnace, which will normally be a mixture consisting primarily of hydrogen, carbon monoxide, and unreacted steam and methane, is passed, preferably without substantial cooling, through lines 88, 36 and 33 into gasifier 32. This stream is the primary source of the hydrogen, carbon monoxide and steam required in the gasifier in addition to the carbon-alkali metal catalyst to produce the thermoneutral reaction that results in the formation of essentially carbon dioxide and methane. It is, therefore, desirable that the reforming furnace effluent contain sufficient carbon monoxide and hydrogen to supply the substantially equilibrium quantities of those gases required in the gasifier and sufficient unreacted steam to provide substantially all of the steam required by the reactions taking place in the gasifier.

For the purposes of thermal efficiency, it is preferable that the steam reforming step of the process be utilized in such a manner as to obviate the need for a separate preheat step. This may be achieved by operating the reforming furnace so that the heat content of the effluent is sufficient to preheat the carbonaceous feed material to gasification temperature and maintain all the reactants at such temperature by compensating for heat losses during gasification. Normally, this may be accomplished if the temperature of the effluent is between about 100° F. and about 300° F. higher than the operating temperature in the gasifier. For optimum thermal efficiency, it is important that the effluent from the steam reforming furnace be passed to the gasifier in such a manner as to avoid substantial cooling.

It will be apparent from the above discussion that the effluent from the reforming furnace 83 will supply substantially all the heat required in gasifier 32. The effluent will not only contain sufficient sensible heat to preheat the carbonaceous feed material to reaction temperature and maintain all the reactants at such temperature by compensating for heat losses during gasification, but it will also contain sufficient amounts of carbon monoxide and hydrogen which react in the gasifier to produce enough exothermic heat to substantially balance the endothermic heat consumed by the reaction of the steam with carbon.

The mixture of carbon monoxide, hydrogen and methane removed overhead from cryogenic unit 76 through line 78 will normally contain only between about 2 mole percent and about 15 mole percent methane. It has been found that this synthesis gas is a suitable feed material for the synthesis of methanol and thus facilitates the integration of catalytic gasification with a methanol synthesis process.

The synthesis gas in line 78 is mixed with carbon dioxide introduced into line 78 through line 89. Normally, the carbon dioxide is obtained from the regeneration of the spent solvent removed from carbon dioxide absorber 68 through line 70. Sufficient carbon dioxide is normally injected into line 78 in order to adjust the carbon oxides to hydrogen ratio and/or activate the methanol synthesis catalyst. The mixture of synthesis gas and carbon dioxide is then combined with a cool recycle stream of hydrogen, carbon monoxide, methane and carbon dioxide introduced into line 78 via line 91, and the combined streams are compressed and passed into methanol synthesis reactor 92. Here the combined gases are passed downwardly through fixed beds of methanol synthesis catalyst at a temperature between about 400° F. and about 700° F., preferably between about 425° F. and about 575° F., and at a pressure between about 400 psig and about 2000 psig. Under these conditions and in the presence of the catalyst, the carbon monoxide and hydrogen in the mixture of gases react to form methanol. The carbon dioxide in the gases may react slowly with hydrogen to form methanol and water or carbon monoxide and water.

The methanol synthesis reactor will normally be comprised of a pressure vessel or series of such vessels each containing a charge of catalyst arranged in a continuous bed or several independently supported beds. The amount of catalyst provided in each reactor will depend on the temperature and pressure employed during the synthesis, the composition of the feed gas to the reactor, and the degree of conversion of the feed gas to methanol in each catalyst bed. The space velocity employed in the reactor will vary from about 5000 to about 50,000, preferably from about 7000 to about 25,000, volumes of dried gas at standard conditions per hour per volume of catalyst.

The catalyst employed in the reactor or reactors will normally be partially reduced oxides of copper, zinc, and chromium; zinc oxide and chromium oxide; zinc oxide and copper; copper and aluminum oxide or cesium oxide; zinc oxide and ferric hydroxide; zinc oxide and cupric oxide; a copper zinc alloy, the oxides of zinc, magnesium, cadmium, chromium, vanadium, and/or tungsten with oxides of copper, silver, iron and/or cobalt; and the like. Either individual catalysts or mixtures of catalysts may be used. The catalyst may be finely ground, pelleted, granular, extruded with a binding agent or in any other suitable form.

The gaseous effluent from methanol synthesis reactor 92, which consists primarily of methanol, unreacted carbon monoxide and hydrogen, and small amounts of carbon dioxide, methane and water is withdrawn through line 93 and passed to heat exchanger 94 where the gases are cooled to condense the methanol and any water formed in the methanol synthesis reactor. The cooled effluent exiting heat exchanger 94 through line 95 is passed to methanol accumulator 96 where the condensed liquids are allowed to separate from the cooled gases. Methanol is removed from the accumulator through line 97 and passed downstream for purification. The degree of purity required for the methanol product will depend upon the end use contemplated for the methanol. If the methanol is to be used directly as fuel, very little, if any, purification may be required.

The cool gas exiting methanol accumulator 96 through line 98 will normally contain between about 20 and about 80 mole percent hydrogen, between about 2 and about 20 mole percent carbon monoxide, between about 20 and about 60 mole percent methane, and a small amount of carbon dioxide. A portion of this gas is normally recycled directly to methanol synthesis reactor 92. In general, between about 75 volume percent and about 97 volume percent of the gas in line 98 is compressed and passed through lines 91 and 100 for reintroduction into methanol synthesis reactor 92. Recycle of this cool gas serves to prevent the temperature in the methanol synthesis reactor from increasing to an undesired value and also allows for further conversion of the carbon monoxide and hydrogen comprising the gas into methanol as the constituents again pass through the reactor.

The portion of the gas in line 98 that is not directly recycled to methanol synthesis reactor 92 through lines 91 and 100 is normally referred to as a purge gas in conventional methanol synthesis processes. This gas is passed through line 99 into line 67 and combined in line 66 with the effluent from hydrogen sulfide absorber 63. The combined gas stream in line 66 is then passed into carbon dioxide absorber 68. In absorber 68 the carbon dioxide in the purge gas is removed and the remaining carbon monoxide, hydrogen and methane are passed, as described previously, to cryogenic distillation unit 76 where a large portion or substantially all of the methane is removed and passed to steam reforming furnace 83. The carbon monoxide and hydrogen originally in the recycle purge gas is withdrawn overhead from the cryogenic distillation unit and recycled through line 78 to methanol synthesis reactor 92.

In conventional methanol synthesis processes, the portion of the methanol synthesis reactor effluent that is not recycled directly to the methanol synthesis reactor is removed as a purge gas in order to prevent carbon dioxide and methane from accumulating rapidly in the reactor and choking the methanol synthesis reactions. This purge gas is normally sold as an intermediate BTU gas. The integration of catalytic gasification with methanol synthesis in accordance with the process of the invention allows this purge gas to be recycled through the carbon dioxide absorption and cryogenic separation steps of the process to remove the carbon dioxide and methane so that the remaining carbon monoxide and hydrogen can be passed back through the methanol synthesis reactor for further conversion into methanol. Thus, the process of the invention results in substantially greater yields of methanol than can be obtained using a conventional methanol synthesis process wherein the carbon monoxide and hydrogen in the purge gas is lost to the process and not recycled to the methanol synthesis reactor.

In the embodiment of the invention described above and shown in the drawing, a cryogenic separation unit is utilized to separate methane from carbon monoxide and hydrogen. It will be understood that the process of the invention is not limited to a cryogenic separation unit and includes any type of separation zone in which a mixture of carbon monoxide, hydrogen and methane is divided into a stream rich in carbon monoxide and hydrogen and a methane-rich stream.

It will be apparent from the foregoing that the invention provides a process for producing methanol via the catalytic gasification of coal and similar carbonaceous feed materials. The process of the invention has advantages over conventional methanol synthesis processes in that it results in higher yields of methanol without sacrificing overall process efficiency.

We claim:

1. A process for the production of methanol from a carbonaceous feed material which comprises:
   (a) gasifying said carbonaceous feed material with steam in a gasification zone at a gasification temperature between about 1000° F. and about 1500° F. and at a gasification pressure in excess of about 100 psia in the presence of a carbon-alkali metal catalyst and added hydrogen and carbon monoxide;
   (b) withdrawing from said gasification zone an effluent gas containing methane, carbon dioxide, steam, hydrogen, carbon monoxide, and hydrogen sulfide;
   (c) treating said effluent gas for the removal of steam, particulates, hydrogen sulfide and carbon dioxide to produce a treated gas containing primarily carbon monoxide, hydrogen and methane;
   (d) passing said treated gas to a separation zone wherein said treated gas is separated into a methane-rich gas stream and a gas stream containing primarily carbon monoxide and hydrogen;
   (e) passing at least a portion of said methane-rich gas stream to a steam reforming zone wherein at least a portion of said methane is reacted with steam to produce hydrogen and carbon monoxide;
   (f) passing the effluent from said steam reforming zone into said gasification zone, thereby supplying said added hydrogen and carbon monoxide required in said gasification zone;
   (g) passing said gas stream containing primarily carbon monoxide and hydrogen produced in step (d) to a methanol synthesis zone wherein at least a portion of said carbon monoxide is reacted with at least a portion of said hydrogen in the presence of a methanol synthesis catalyst to form methanol;
   (h) recovering methanol product from the effluent stream exiting said methanol synthesis zone, thereby leaving a gas comprised of carbon monoxide, hydrogen, methane and carbon dioxide; and
   (i) recycling at least a portion of said gas comprised of carbon monoxide, hydrogen, methane and carbon dioxide produced in step (h) to the separation zone of step (d).

2. A process as defined by claim 1 wherein said carbonaceous feed material comprises coal.

3. A process as defined by claim 2 wherein said carbon-alkali metal catalyst is prepared by treating said coal with an alkali metal compound or compounds and thereafter heating the coal to said gasification temperature in said gasification zone.

4. A process as defined by claim 1 wherein the portion of said gas comprising carbon monoxide, hydrogen, methane and carbon dioxide produced in step (h) that is recycled to the separation zone of step (d) is first treated for the removal of carbon dioxide.

5. A process as defined by claim 4 wherein said portion of said gas is treated for the removal of carbon dioxide by recycling said gas to step (c).

6. A process as defined by claim 1 wherein at least a portion of the gas comprising carbon monoxide, hydrogen, methane and carbon dioxide produced in step (h) is recyled directly to said methanol synthesis zone.

7. A process as defined by claim 1 wherein the gas stream containing primarily carbon monoxide and hydrogen produced in step (d) is mixed with carbon dioxide removed from the effluent gas from said gasification zone in step (c) prior to passing said gas stream containing primarily carbon monoxide and hydrogen to said methanol synthesis zone.

8. A process as defined by claim 1 wherein a portion of said methane-rich gas stream is used as fuel for said steam reforming zone.

9. A process as defined by claim 1 wherein between about 75 and about 97 volume percent of the gas comprising carbon monoxide, hydrogen, methane and carbon dioxide produced in step (h) is recycled directly to said methanol synthesis zone and the remaining portion of said gas is recycled to the separation zone of step (d).

10. A process for the production of methanol from coal which comprises:

(a) gasifying said coal with steam in a gasification zone at a temperature between about 1200° F. and about 1400° F. and at a pressure between about 200 psia and about 800 psia in the presence of a carbonalkali metal catalyst and added hydrogen and carbon monoxide;

(b) withdrawing from said gasification zone an effluent gas containing methane, carbon dioxide, steam, hydrogen, carbon monoxide and hydrogen sulfide;

(c) treating said effluent gas for the removal of steam and particulates to produce a treated gas containing primarily carbon monoxide, hydrogen, methane, carbon dioxide and hydrogen sulfide;

(d) removing said hydrogen sulfide from said treated gas to produce a substantially hydrogen sulfide-free gas;

(e) combining said substantially hydrogen sulfide-free gas from step (d) with a recycle gas containing carbon monoxide, hydrogen, methane and carbon dioxide to form a combined gas stream comprised primarily of carbon monoxide, hydrogen, methane and carbon dioxide;

(f) treating said combined gas stream to remove carbon dioxide and thereby produce a treated gas containing primarily carbon monoxide, hydrogen and methane;

(g) passing said treated gas from step (f) to a cryogenic separation zone wherein said treated gas is separated into a methane-rich gas stream and a gas stream containing primarily carbon monoxide and hydrogen;

(h) passing at least a portion of said methane-rich gas stream to a steam reforming zone wherein at least a portion of said methane is reacted with steam to produce hydrogen and carbon monoxide;

(i) passing the effluent from said steam reforming zone into said gasification zone, thereby supplying said added hydrogen and carbon monoxide required in said gasification zone;

(j) passing said gas stream containing primarily carbon monoxide and hydrogen produced in step (g) to a methanol synthesis zone wherein at least a portion of said carbon monoxide is reacted with at least a portion of said hydrogen in the presence of a methanol synthesis catalyst to form methanol;

(k) recovering methanol product from the effluent stream exiting said methanol synthesis zone, thereby leaving a gas comprised of carbon monoxide, hydrogen, methane and carbon dioxide;

(l) recycling a portion of said gas produced in step (k) directly to said methanol synthesis zone; and (m) using the remainder of said gas produced in step (k) as said recycle gas in step (e).

11. A process as defined by claim 10 wherein said cryogenic separation zone in step (g) comprises a cryogenic distillation column.

* * * * *